United States Patent [19]
Inoue

[11] Patent Number: 6,103,124
[45] Date of Patent: *Aug. 15, 2000

[54] ORGANIC WASTE PROCESSOR AND ORGANIC WASTE PROCESSING METHOD

[75] Inventor: Takakazu Inoue, Ushiku, Japan

[73] Assignee: Sanyo Electric Co., Ltd., Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/936,016

[22] Filed: Sep. 23, 1997

[30] Foreign Application Priority Data

Sep. 26, 1996 [JP] Japan ................................. 8-254950
Sep. 22, 1997 [JP] Japan ................................. 9-256596

[51] Int. Cl.$^7$ ........................................................... C02F 3/02
[52] U.S. Cl. .......................... 210/614; 210/616; 210/620
[58] Field of Search .................................. 210/143, 150, 210/151, 209, 220, 613, 614, 615, 616, 617, 620

[56] References Cited

U.S. PATENT DOCUMENTS

| | | | |
|---|---|---|---|
| 4,062,770 | 12/1977 | Kneer | 210/614 |
| 4,663,045 | 5/1987 | Yengley | 210/614 |
| 4,684,468 | 8/1987 | Debaerc | 210/613 |
| 5,080,793 | 1/1992 | Urlings | 210/617 |
| 5,451,319 | 9/1995 | Kobayashi | 210/613 |
| 5,527,464 | 6/1996 | Burtha et al. | 210/613 |
| 5,601,720 | 2/1997 | Schmid | 210/614 |
| 5,622,617 | 4/1997 | Tsusaka et al. | 210/614 |

FOREIGN PATENT DOCUMENTS

| | | |
|---|---|---|
| 0606617 | 7/1994 | European Pat. Off. . |
| 588683 | 12/1993 | Japan . |
| 057458 | 3/1995 | Japan . |
| 057458 | 3/1996 | Japan . |
| 8243528 | 9/1996 | Japan . |
| 8243532 | 9/1996 | Japan . |
| 8276169 | 10/1996 | Japan . |

*Primary Examiner*—Christopher Upton
*Attorney, Agent, or Firm*—Hogan & Hartson LLP

[57] ABSTRACT

To provide an organic waste processor wherein the formation of lumps of processing material is suppressed, and wherein the processing material can be used for a long time period. An organic waste processor 10 comprises a processing tank 12 for processing organic waste, such as kitchen waste. The processing tank 12 contains a material 11 on which microorganisms are supported which aerobically decompose kitchen waste. By sending air from an air pump 20 into the processing tank 12, the water content of the material 11 is decreased, and the formation of lumps due to sticking together of the processing material 11 is thereby suppressed.

4 Claims, 3 Drawing Sheets

ORGANIC WASTE PROCESSOR AND ORGANIC WASTE PROCESSING METHOD

BACKGROUND OF THE INVENTION

1. Field of the Invention

This invention relates to an organic waste processor and processing method, and in particular to an organic waste processor and processing method in which organic waste is processed using a processing material upon which microorganisms are supported.

2. Description of the Related Art

In general, organic waste discharged from homes is collected separately as raw garbage or burnable garbage by local public bodies, burnt, and then buried. In this waste disposal system, however, a problem is now arising in that a large amount of manpower is required to collect the waste and a large area is required to bury it.

To resolve this problem, an organic waste processor suitable for the home which uses microorganisms to convert organic waste to compost is commercially available. The compost-like product of this organic waste processor may for example be re-used as fertilizer for home vegetable gardens.

However this processor merely converts organic waste into a compost-like product, and does not destroy the waste. It was therefore unsuitable for homes which did not have the capacity to re-use the product.

In recent years, devices have been proposed wherein, after converting the organic waste to a compost-like product, it was further decomposed into low molecular weight products such as water or carbon dioxide gas, e.g. as disclosed in Japanese Utility Model Laid-Open Publication Hei 5-88683 (Koho). According to this method, microorganisms having decomposing ability were supported on special wood chips as a processing material, the water content of this material was maintained at approximately 63%, and organic waste was then mixed with it and stirred. Due to the stirring, the microorganisms were aerobically cultivated, and the organic waste was accordingly digested and decomposed into low molecular weight products such as water and carbon dioxide. Consequently, in a device functioning according to this method, the organic waste is effectively completely destroyed, and it may therefore conveniently be used even when there is no ability to dispose of compost.

However as described above, in a device which decomposes and digests organic waste while maintaining the water content of the processing material at 65%, after a long period of use such as for example 3 months, the processing material in the device sticks together to form lumps. It appears that when decomposition products adhere to the processing material and a certain amount of water is added, these products become viscous and cause the material to lump together.

When the processing material sticks together and forms lumps, the microorganisms contained in the material are unable to grow aerobically. At the same time, their contact with the organic waste is prevented so that their ability to digest and decompose the waste declines. Also, although the microorganisms supported on the processing material cannot grow aerobically, they do grow under anaerobic conditions. When microorganisms grow under anaerobic conditions in this way, a characteristic foul odor is produced. Hence using conventional processing materials, it was necessary to regularly replace the material.

This invention, which was conceived in view of the above problems, therefore aims to suppress the water content of the processing material so as to suppress the formation or development of lumps due to sticking together of processing material, thereby providing an organic waste processor in which the processing material can be used for a long time period.

It is a further object of this invention to provide an organic waste processor wherein, as a result of adjusting the water content of the processing material by controlling air circulation, the pH or salt concentration in the processing tank can be maintained at such a level as to suppress the proliferation of bacteria that cause food poisoning.

SUMMARY OF THE INVENTION

To resolve the above problems, the organic waste processor according to this invention which uses microorganisms to digest and decompose organic waste, for example kitchen waste, comprises a processing material for supporting microorganisms, a processing tank in which organic waste is processed by the processing material, and a water content adjusting means for adjusting the water content of the processing material, the water content of the processing material being adjusted by the water content adjusting means so as to control it to lie within such a range that the formation of lumps due to sticking together of processing material is suppressed.

The microorganisms supported on the processing material may be either pre-adsorbed on the processing material or adsorbed by natural generation. The term "natural growth" refers to microorganisms which proliferate without performing any special inoculation, including the case where microorganisms adhering to organic waste enter the processor and proliferate during waste processing.

In the context of this invention, the water content in which the processing material is conveniently ranges from approximately 35% to approximately 45%.

According to the above construction, the water content of the processing material is maintained by the water content adjusting means at such a proportion that the formation of lumps due to sticking together of processing material is suppressed, and preferably inhibited. As a result, aerobic growth of the microorganisms supported on the processing material is ensured without replacing the processing material for a long time period, and organic waste may be efficiently digested and decomposed. Also according to this construction, the problem which occurred when lumps were formed as described above, i.e. the foul odor produced when the microorganisms grew under anaerobic conditions, is prevented.

According to this invention, the water content adjusting means comprises a circulating means which adjusts the water content of the processing material by causing air to circulate inside the processing tank.

Normally, when organic waste is digested and decomposed, water is produced as a decomposition product, and if processing of waste is continued in this state, the water content of the processing material rises. However according to this invention, air is made to circulate inside the processing tank by the circulating means so that excess humidity, i.e. moisture, is removed, and the water content of the processing material is thereby maintained within such a range that the formation of lumps due to sticking together of processing material is suppressed, and preferably inhibited.

Moreover when the water content adjusting means adjusts the water content by removing only moisture by circulation, it is easy to suitably adjust the internal salt concentration or pH. This is because, as only moisture is removed by the circulating means, salt concentration, etc., is maintained during the adjustment. As a result, the interior of the processing tank can be maintained at a high salt concentration or high pH. By adjusting for example either the pH or salt concentration in the processing tank, or both, an environment is therefore created inside the processing tank in which the growth of bacteria that cause food poisoning can be inhibited. In this way, organic waste can be processed while the growth of such bacteria is suppressed.

According to this invention, it is moreover desirable that a stirring means is provided to stir the processing material in the processing tank.

According to this invention, the processing material is stirred by the stirring means, and the microorganisms supported on processing materials are brought into uniform contact with air. This prevents the water content in the material from being uneven, and promotes the aerobic growth of the microorganisms.

DESCRIPTION OF THE PREFERRED EMBODIMENT

A preferred form of the invention will now be described in detail with reference to the drawings.

Figure 1:
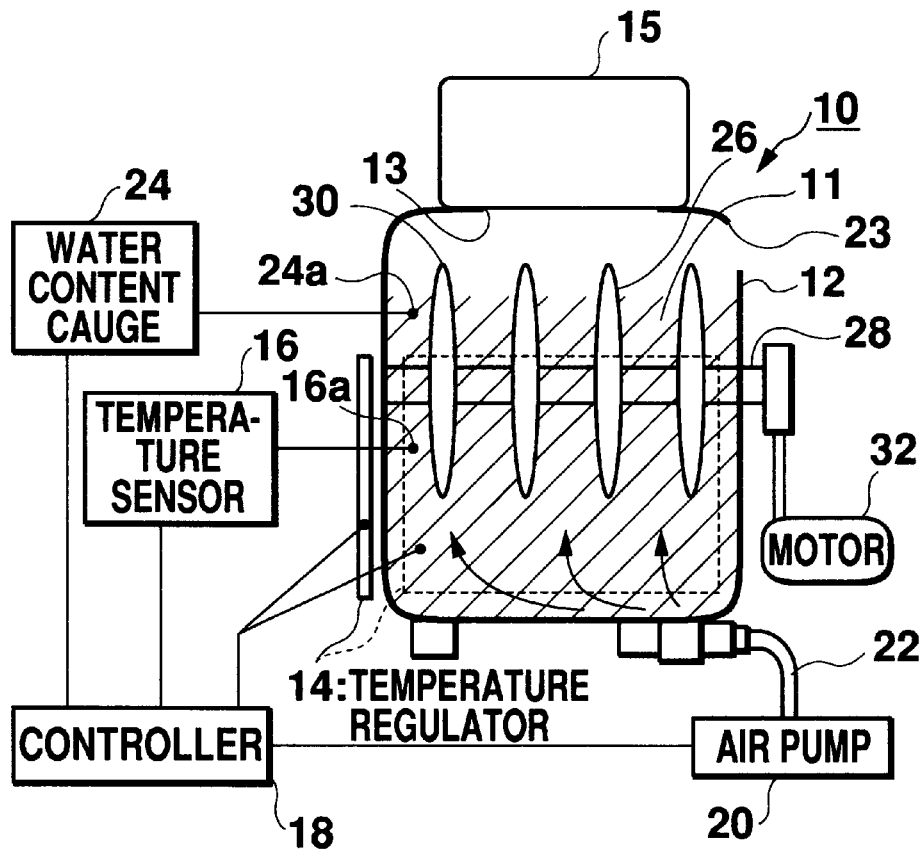
FIG. 1 is a diagram showing the overall construction of an organic waste processor according to one form of this invention.

FIG. 1 shows the overall construction of an organic waste processor 10 according to this form of the invention.

This organic waste processor 10 comprises a processing tank 12 containing a processing material 11, described hereafter, for digesting and decomposing organic waste, for example kitchen waste. An inlet port 13 for introducing organic waste is provided inside the processing tank 12. This inlet port 13 is provided with a cap 15, the port 13 being covered by this cap 15 while organic waste is being decomposed.

The processing material 11 in the processing tank 12 comprises predetermined microorganisms supported on wood chips, for example shavings of Japanese cedar. Specifically, these predetermined microorganisms are a bacteria which can be grown under aerobic conditions, or a plurality of bacteria which grow naturally when raw garbage is aerobically decomposed. Also as will be described hereafter, the environment in the processing tank may be adjusted so that the plurality of naturally-growing bacteria excludes undesirable bacteria that cause food poisoning. In this context, the term "natural growth" refers to bacteria which proliferate without performing any special inoculation, including the case where bacteria adhering to organic waste enter the processor and proliferate during waste processing.

A temperature adjusting device 14 is provided in the processing tank 12 to adjust the internal temperature of the tank 12 when organic waste is being processed. This temperature adjusting device 14 completely surrounds the tank 12 so as to maintain the temperature inside the tank at or above a predetermined temperature. There is no limitation on the construction of this temperature adjusting device 14 provided that it can maintain the temperature inside the tank 12 uniform.

A temperature sensor 16 is connected to the temperature adjusting device 14 via a controller 18. A temperature detector 16a of the temperature sensor 16 is installed in the tank 12 to measure the internal temperature of the tank 12. This internal temperature is sent to a controller 18 which controls the operation of the temperature adjusting device 14, and the internal temperature of the tank 12 is thereby maintained within a predetermined temperature range. This predetermined temperature may be set to a suitable growth temperature for these microorganisms.

An air pump 20 is provided in the tank 12 as a circulating means to adjust the water content of the processing material by circulation. This air pump 20 comprises a ventilation duct 22 for sending air into the processing tank 12, and this ventilation duct 22 is connected to the base of the processing tank 12. Air from the air pump 20 is thereby sent as a rising flow inside the tank 12 via the ventilation duct 22. Due to this air which is blown in, the microorganisms supported on the processing material 11 are able to grow aerobically, and part of the moisture is removed from the processing material 11. This moisture is discharged from a discharge port 23.

Due to this air pump 20, the water content of the processing material 11 is controlled to such a proportion that the formation or development of lumps due to sticking together of the material 11 is suppressed. A water content gauge 24 is connected to the pump 20 via the controller 18. A water content measuring unit 24a of this water content gauge 24 is installed in a position where it is in contact with the processing material 11 inside the tank 12, and measures the water content of this processing material 11. The water content measured here is sent to the controller 18, and the controller 18 which receives this measured value suitably adjusts the ventilation rate from the air pump 20. In the aforesaid construction, from experimental results to be described in detail hereafter, the water content of the processing material 11 at which the formation of lumps due to sticking together of the processing material 11 is suppressed preferably lies in a range from approximately 35% to approximately 45%, but is more preferably approximately 40%.

In the aforesaid construction, air from the air pump 20 is sent as a rising flow into the tank 12 via the ventilation duct 22, but the ventilation duct 22 may also be connected above the tank 12 and air sent as a descending flow into the tank 12.

To regulate the water content of the processing material 11, in addition to the circulating means, the water content of the processing material may be adjusted by a heating means. In this case the heating means may be combined with the aforementioned circulating means such as the air pump 20, the water content of the material 11 adjusted by the heating means, and aerobic growth of the microorganisms ensured by the circulating means.

Figure 2:
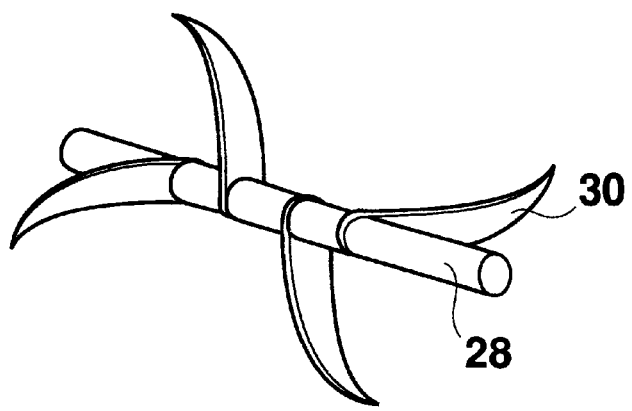
FIG. 2 is a partially expanded view of an organic waste processor according to one form of this invention.

A stirrer 26 is provided in the tank 12 to stir the processing material I1 in the tank 12 so as to make the environment surrounding the material uniform. This stirrer 26 is provided with a rotation shaft 28 suspended inside the tank 12, and a plurality of paddle-shaped stirrer blades 30 are installed on the shaft 28 as shown in FIG. 2. One end of this shaft 28 projects outside the tank 12, a motor 32 being provided on this projecting end. The shaft 28 is rotated by driving this motor 32, and this causes the blades 30 to rotate in synchronism.

The action of the aforesaid organic waste processor 10 will now be described.

When organic waste is to be processed, the waste is introduced into the tank 12 containing the processing material 11 from the inlet 13, and the processor is closed by the cap 15. The temperature in the tank 12 into which the organic waste has been introduced, is maintained at a predetermined value, for example within the range 20–70° C., preferably 30–70° C., air is blown in from the air pump 20, and the processing material 11 and organic waste are mixed by the stirrer 26.

Under these predetermined processing conditions, the microorganisms supported on the material 11 grow aerobically due to the air blown in from the air pump 20, and the waste in contact with the microorganisms is aerobically decomposed. When the waste is aerobically decomposed, low molecular weight products such as water, carbon dioxide and ammonia are generated. Gases which are produced such as carbon dioxide and ammonia are removed from the discharge outlet 23. Water on the other hand is absorbed by the material 11, and the water content of the material 11 therefore increases. When the water content of the material 11 increases, the water content gauge 24 detects this increase, and the ventilation rate of the air pump 20 is increased. The water content of the material 11 is thereby decreased so that it is maintained at a level at which formation of the aforesaid lumps is suppressed. This sequence of digestion and decomposition operations is repeated each time organic waste is introduced.

As described hereabove, according to this form of the invention, the water content of the processing material 11 is kept at a proportion where the formation of lumps due to sticking together of the processing material is suppressed, i.e. 35%–45%, unlike the prior art. The processing material can therefore be used repeatedly over a long time period. Moreover, since the water content of the processing material is adjusted so that formation of lumps is suppressed as described hereabove, anaerobic growth of microorganisms can be prevented. The foul odor arising due to the growth of microorganisms can therefore be avoided.

Moreover according to this form of the invention, as a circulating means is employed to remove moisture contained in the processing material 11, the environment in the processing tank 12, in particular salt concentration and pH, maybe adjusted as desired. Hence the proliferation of undesirable bacteria, in particular bacteria that cause food poisoning, may be suppressed by adjusting the salt concentration and pH in the tank 12.

According to the organic waste processor of this invention, water content of a processing material is maintained within such limits that the formation of lumps due to sticking together of processing material is suppressed. There is therefore no loss of waste processing efficiency due to lumping of processing material, and the processing material may be used for a long time period.

Moreover, as lumping of processing material is suppressed as described hereabove, other problems due to this lumping, specifically the foul odor produced when microorganisms supported on the processing material grow anaerobically, are avoided.

At the water content used in this invention, all the water in the processing material is vaporized, so waste water is not discharged from the processor.

Moreover, waste can be efficiently processed even when the processing tank is maintained at a high salt concentration and high pH. Organic waste may thus be processed while the proliferation of bacteria that cause food poisoning such as *E. coli*, which requires a low salt concentration and neutral pH, is suppressed.

This invention will now be described in further detail with reference to specific examples.

EXAMPLE 1

The aforesaid organic waste processor was designed to process the amount of raw garbage normally discharged by a family of 4, i.e. an average of 1 kg per day (approximately 0.15 kg as dry weight).

Specifically, the dimensions of the processing tank were 580×450×795 mm, and this processing tank contained 8 kg of processing material in terms of dry weight. As processing conditions, the internal temperature of the processing tank was maintained at 30 degrees or above by a thermostat, and 1 kg of garbage was digested and decomposed every day for 343 days while the processing material was stirred by a stirrer.

Figure 3:
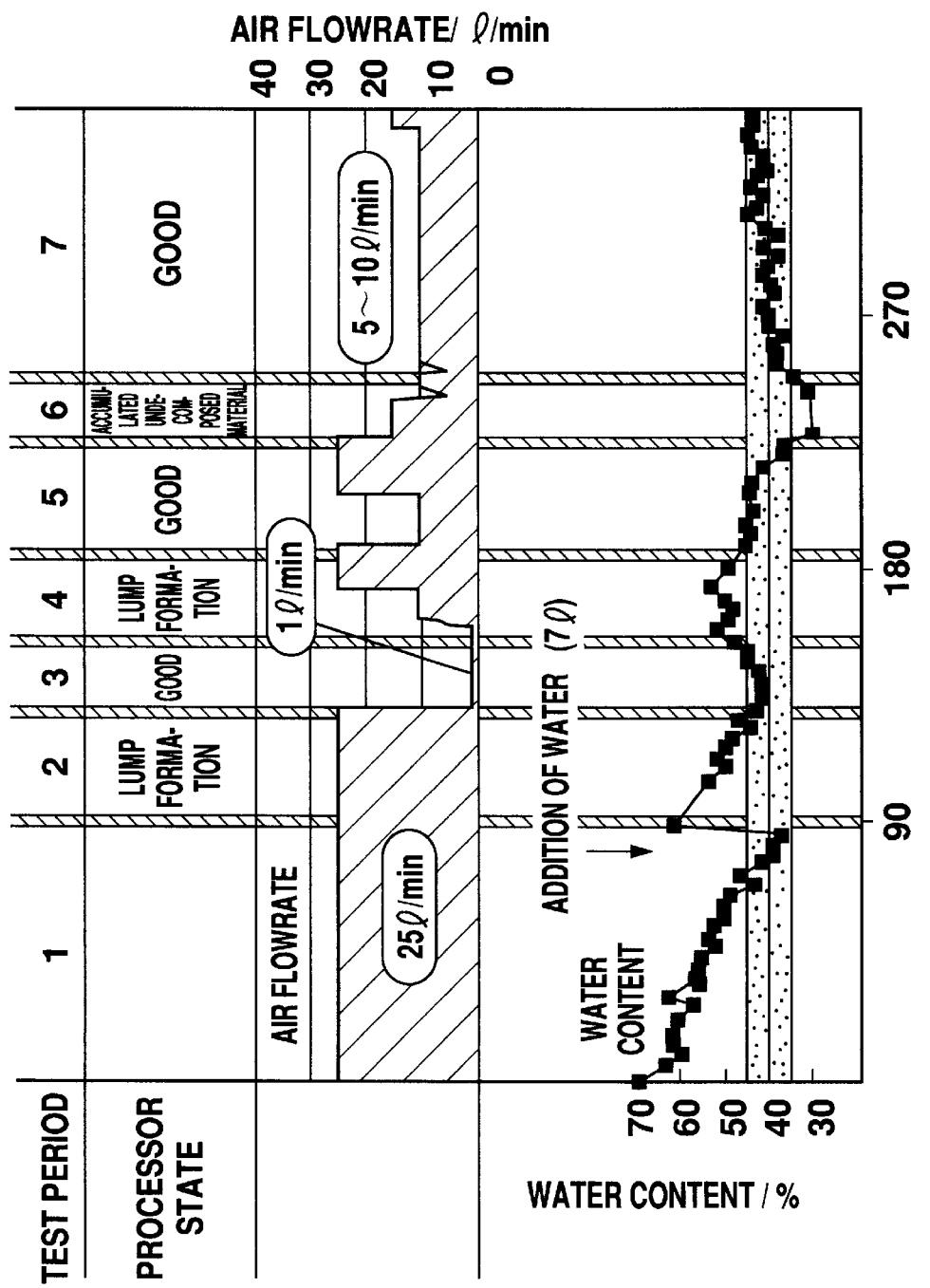
FIG. 3 is a graph showing the conditions in a processing tank when waste is digested and decomposed for a period of 343 days according to the first example.

FIG. 3 shows the state of the processing material, and in particular the presence or absence of the aforementioned lumps, which was obtained during digestion and decomposition over the period of 343 days when the amount of air blown in from an air pump was varied so as to vary the water content of the processing material.

As shown in FIG. 3, the air circulation rate from the pump was fixed at 25 l/min for approximately 140 days from the start of the experiment (Experimental Periods 1 and 2). Part of the water produced by digestion and decomposition and absorbed by the processing material was removed, and the water content of the processing material adjusted. When the air circulation rate was 25 l/min, the initial water content of 70% fell to approximately 35% in 90 days, and it was found that a constant water content could not be maintained at this air circulation rate. Subsequently, after adding approximately 7 liters of water, the air circulation rate was set to various levels from 1 liter/min to 25 liter/min, and the water content and state of the processing material were examined.

During Periods 2 and 4, the water content of the processing material exceeded 45%, and the material was observed to form lumps. On the other hand during Period 6 when the water content fell to about 30%, the material did not form lumps, but as decomposition of the organic waste was inadequate, unprocessed waste was observed to accumulate.

During Periods 3 and 5, the water content was maintained at from approximately 40% to approximately 45%. In this state, lumps of processing material were not observed, there was no remaining undecomposed waste, and good results were obtained. In particular during Period 5 when the air circulation rate was 10 liter/min, the water content stabilized at approximately 45%. Subsequently, in Period 7, the air circulation was fixed at 10 liter/min. The water content of the processing material and lumping of material were examined over a period of approximately 100 days. As a result, the water content was stable at from approximately 35% to approximately 45%, and at this water content, formation of the aforementioned lumps was not observed.

It was therefore found that for a processing tank of the aforesaid size and the aforesaid amount of processing material, the air circulation rate may conveniently be 10 liter/min for a rising flow. This circulation rate must be varied as necessary depending on the size and the temperature of processing tank and the amount of processing material.

Figure 4:
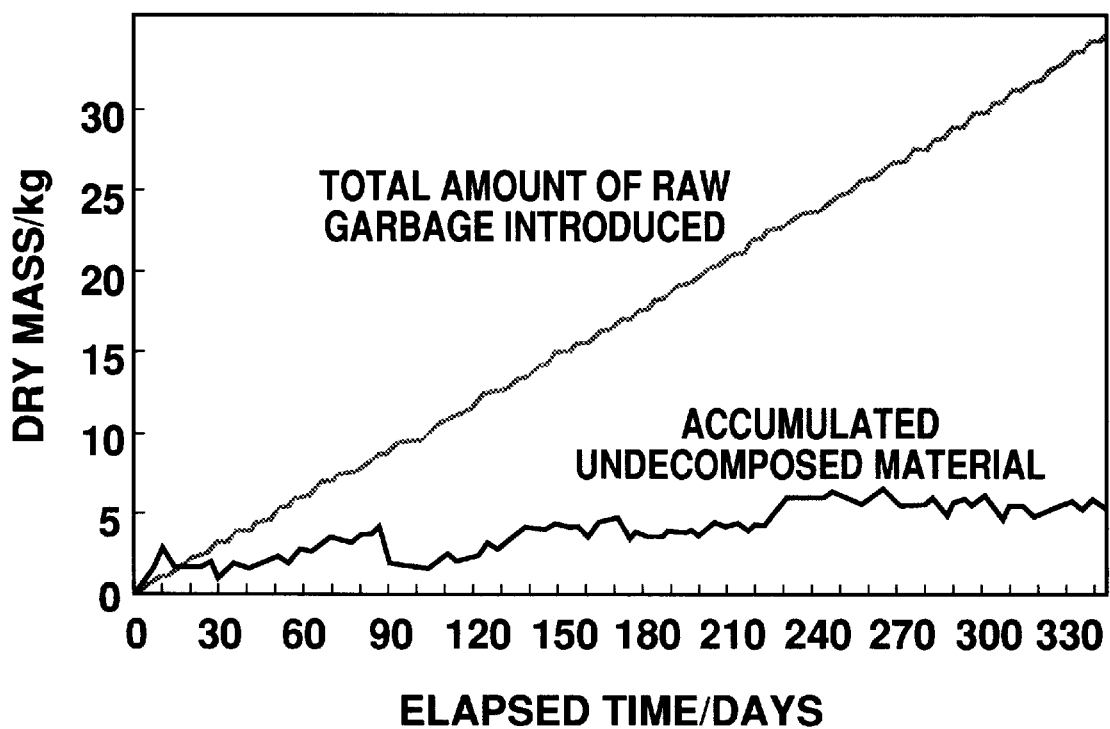
FIG. 4 is a graph showing the accumulated undecomposed material in the processing tank when waste is digested and decomposed for a period of 343 days according to the first example.

FIG. 4 shows the accumulated undecomposed material as dry weight remaining in the processing tank after the 343 day period mentioned above. In FIG. 4, the total amount of raw garbage introduced and accumulated undecomposed material are shown as dry weight. The accumulated undecomposed material is substantially constant regardless of the total amount of raw garbage introduced, as seen in the figure. This means that the raw garbage was effectively completely digested and decomposed into low molecular weight products, and that these low molecular weight products, e.g. ammonia, carbon dioxide and water, were removed from the processing tank.

From the above experimental results, it is clear that the water content of the processing material must be maintained at or below approximately 45% to suppress formation of lumps of the material, and that the water content of the processing material must be approximately 35% or higher to process the garbage without forming undecomposed products.

In this way, by maintaining the water content of the processing material at approximately 35%–approximately 45%, raw garbage could be effectively digested and decomposed over a long time period (at least 343 days) while formation of lumps of processing material was suppressed, and without the need to replace the processing material.

EXAMPLE 2

Table 1 and Table 2 show the results of examining the contents of the processing tank after 9 months (approximately 270 days) had elapsed during the aforesaid 343 day period.

To examine the contents of the tank, the processing material was sampled, the sample was suspended in pure water, and the electrical conductance and pH of the suspension were measured.

When processing was begun, the contents of the tank contained almost no salts and the pH was neutral, but after 270 days processing, there was a high salt concentration and high pH. This may be considered to be due to decomposition products from the digestion and decomposition of kitchen waste, e.g. ammonia and various salts, etc., which had remained and accumulated in the processing tank.

Next, the growth of bacteria under these high salt concentration, high pH conditions was investigated.

In Table 1, agar plates were prepared with various combinations of salt concentration and pH, and bacteria supported on processing material were grown on the agar plates to identify the conditions suitable for bacterial growth. The results were classified based on the number of colonies (colony forming units) found on the agar plates.

As shown in Table 1, after approximately 270 days, more colonies were obtained on agar plates with a pH of 9 or higher and a salt concentration of 0.25–1.0M NaCl. This shows that whereas a large number of bacteria grew well at 0.25M NaCl and pH 7 at the start of processing, bacteria to which a high salt concentration and high pH were suited increased after approximately 270 days due to the change of salt concentration and pH in the processing tank.

TABLE 1

| NaCl/M | pH 5 | pH 7 | pH 9 | pH 11 |
|---|---|---|---|---|
| 0.25 | $3.7 \times 10^8$ | $7.5 \times 10^9$ | $2.4 \times 10^{10}$ | $2.1 \times 10^{10}$ |
| 0.5 | $9.1 \times 10^7$ | $1.0 \times 10^{10}$ | $3.2 \times 10^{10}$ | $2.2 \times 10^{10}$ |
| 1.0 | $2.6 \times 10^6$ | $8.4 \times 10^9$ | $2.8 \times 10^{10}$ | $1.4 \times 10^{10}$ |
| 2.0 | $<10^4$ | $1.1 \times 10^9$ | $1.1 \times 10^9$ | $2.4 \times 10^8$ |

Also, of those bacteria supported on the processing material after approximately 270 days processing, the main bacteria were grown on respectively two types of agar plates (low salt concentration, neutral pH agar plate, and high salt concentration, high pH agar plate), and the conditions more suitable for growth were examined based on the size of the colonies. Table 2 shows the results. For the low salt concentration, neutral pH agar plate, a 0.085M NaCl, pH 7 bouillon agar plate was used, and for the high salt concentration, high pH agar plate, a 0.5M NaCl, pH 9 Bion agar plate was used.

As shown in Table 2, on a high salt concentration, high pH agar plate, 84.7% of the bacteria formed large colonies, and not many bacteria grew well on a low salt concentration, neutral pH agar plate. The latter type of bacteria were conventionally used for processing kitchen waste.

TABLE 2

| COLONY SIZE COMPARISON | |
|---|---|
| pH 9, 0.5M NaCl > pH7, 0.085M NaCl | 84.7% |
| pH 9, 0.5M NaCl = pH7, 0.085M NaCl | 3.1% |
| pH 9, 0.5M NaCl < pH7, 0.085M NaCl | 12.2% |

From the above results it is seen that after approximately 270 days, instead of the bacteria which were conventionally used for processing kitchen waste, bacteria that grow well at high salt concentration and high pH increase, and the waste is processed by these types of bacteria.

Using this result, i.e. using the fact that organic waste can be processed by bacteria for which a high salt concentration and high pH are suitable, it is evident that processing of waste may be performed while suppressing proliferation of bacteria that cause food poisoning such as $E.$ $coli.$ Most bacteria that cause food poisoning such as $E.$ $coli$ grow well in the medium with low salt concentration, neutral pH, hence the growth of $E.$ $coli$, etc., may be suppressed by increasing either the salt concentration or pH, or both, in the processing tank.

The following techniques may be used to increase the salt concentration or pH in the processing tank.

For example, in an organic waste processor wherein water is removed from the processing tank by an air circulating means or a heating means, the salt concentration or pH may be increased by adding suitable salts or pH regulating agents to the processing tank. The salt concentration or pH may also be increased by allowing digestion and decomposition products of the organic waste to accumulate.

As described above, by adjusting the salt concentration and pH in the processing tank, conditions unfavorable to the growth of bacteria that cause food poisoning are created.

In the organic waste processor according to this invention, processing material may be used for a long time period without replacement by adjusting the water content of the material. However, it is preferable to adjust the conditions in the processing tank, specifically the salt concentration and pH, so as to suppress undesirable proliferation of bacteria that cause food poisoning during this long time period.

The above invention has been described in the context of its application to complete treatment of waste, however it will be understood that it may be applied also to composting and re-use of products from waste in the process of being treated.

What is claimed is:

1. A method for decomposing organic waste by microorganisms, comprising:

blending a processing material with said organic waste in a processing tank, and blending together said organic waste and said processing material while maintaining the water content of said processing material from approximately 35% to approximately 45%, wherein the formation of lumps due to sticking together of said processing material is suppressed and the accumulation of decomposed material is substantially constant, and wherein organic waste introduced daily is continuously decomposed and processed for at least ninety days without replacing or adding the processing material.

2. A method for operating an organic waste processor which uses microorganisms to decompose organic waste, the organic waste processor comprising a processing material for supporting microorganisms, a processing tank for containing the processing material, a stirring unit for stirring the processing material in the tank, and a water content adjusting unit for adjusting the water content of the processing material, the method comprising:

determining whether the processing material form lumps; and adjusting the water content adjusting unit to reduce the water content of the processing material if lumps are formed, the water content of the processing material being approximately 35% to 45%, and wherein organic waste introduced daily is continuously decomposed and processed for at least ninety days without replacing or adding the processing material.

3. The method of claim 2, wherein the water content adjusting unit comprise an air circulating device for providing air to the tank, and wherein the step of adjusting the water content comprises adjusting the amount of air provided to the tank by the air circulating device.

4. A method for decomposing an organic waste, comprising:

blending a processing material containing microorganisms with the organic waste in a processing tank;

removing moisture from the blend to control the water content of the blend to be approximately 35 to 45%; and permitting decomposition products of the organic waste to accumulate in the tank to increase the salt concentration and/or to change the pH of the blend, wherein organic waste introduced daily is continuously decomposed and processed for at least ninety days without replacing or adding the processing material.

* * * * *